US008182589B2

(12) United States Patent
Jha et al.

(10) Patent No.: US 8,182,589 B2
(45) Date of Patent: May 22, 2012

(54) ACETYLENE PROCESS GAS PURIFICATION METHODS AND SYSTEMS

(75) Inventors: Praveen Jha, Longmont, CO (US);
Joseph V. Vininski, Boulder, CO (US)

(73) Assignee: Matheson Tri-Gas, Inc., Basking Ridge, NJ (US)

( * ) Notice: Subject to any disclaimer, the term of this patent is extended or adjusted under 35 U.S.C. 154(b) by 287 days.

(21) Appl. No.: 12/631,017

(22) Filed: Dec. 4, 2009

(65) Prior Publication Data
US 2010/0154630 A1    Jun. 24, 2010

Related U.S. Application Data

(60) Provisional application No. 61/120,261, filed on Dec. 5, 2008.

(51) Int. Cl.
*B01D 8/00* (2006.01)
(52) U.S. Cl. ............................... 95/288; 62/617; 62/55.5
(58) Field of Classification Search ................ 95/15, 23, 95/90, 143, 288, 228–229, 237, 240; 96/242, 96/266, FOR. 112; 62/617, 55.5
See application file for complete search history.

(56) References Cited

U.S. PATENT DOCUMENTS

| | | | | |
|---|---|---|---|---|
| 2,059,120 A * | 10/1936 | Kreuzer et al. | ................. | 4/685 |
| 2,077,310 A * | 4/1937 | Cushing | ........................ | 62/617 |
| 2,236,963 A * | 4/1941 | Babcock et al. | ............... | 62/631 |
| 3,405,192 A * | 10/1968 | Kruis et al. | ................... | 585/259 |
| 3,465,501 A * | 9/1969 | Conseiller et al. | ............. | 95/199 |
| 5,858,065 A | 1/1999 | Li et al. | | |
| 6,110,258 A | 8/2000 | Fraenkel et al. | | |
| 6,425,946 B1 | 7/2002 | Funke et al. | | |
| 6,461,411 B1 | 10/2002 | Watanabe et al. | | |
| 6,491,884 B1 | 12/2002 | Faller et al. | | |
| 6,579,343 B2 | 6/2003 | Brennecke et al. | | |
| 6,733,734 B2 | 5/2004 | Watanabe et al. | | |

(Continued)

FOREIGN PATENT DOCUMENTS

JP    62-019539 A    1/1987

(Continued)

OTHER PUBLICATIONS

PCT International Search Report and Written Opinion mailed Jun. 22, 2010; International Application No. PCT/US2009/066812, 11 pages.

(Continued)

*Primary Examiner* — Duane Smith
*Assistant Examiner* — Ives Wu
(74) *Attorney, Agent, or Firm* — Kilpatrick Townsend & Stockton LLP

(57) ABSTRACT

Methods and systems of purifying an acetylene process gas are described. The methods may include the steps of providing an acetylene vessel containing source acetylene mixed with a solvent impurity, and flowing the source acetylene through a purification container that holds a cooled purifying medium, where at least a portion of the solvent impurity in the source acetylene separates as a liquid impurity on the purifying medium. The method may also include removing the liquid from the purification container and flowing a purified acetylene gas from the purification container. The purified acetylene gas has a concentration of the solvent impurity of about 5 vol. % or less, and the separated liquid impurity is removed without interrupting the flow of the acetylene while the purified acetylene gas flows from the purification container to keep the concentration of the solvent impurity substantially constant in the purified acetylene gas.

16 Claims, 6 Drawing Sheets

U.S. PATENT DOCUMENTS

| | | | |
|---|---|---|---|
| 6,755,892 B2 | 6/2004 | Nalette et al. | |
| 6,783,576 B2 | 8/2004 | Funke et al. | |
| 6,783,577 B2 | 8/2004 | Funke et al. | |
| 6,790,358 B2 | 9/2004 | Funke et al. | |
| 7,314,506 B2 * | 1/2008 | Vininski et al. | 95/114 |
| 2001/0022135 A1 | 9/2001 | Murai | |
| 2002/0178923 A1 | 12/2002 | Kishovich et al. | |
| 2003/0209142 A1 | 11/2003 | Schimkat et al. | |
| 2004/0069144 A1 | 4/2004 | Wegeng et al. | |
| 2004/0206241 A1 | 10/2004 | Tempel et al. | |
| 2006/0086247 A1 | 4/2006 | Vininski et al. | |
| 2008/0237131 A1 | 10/2008 | Brown et al. | |
| 2008/0242912 A1 | 10/2008 | Letessier et al. | |
| 2009/0173396 A1 * | 7/2009 | Spadavecchia | 137/357 |

FOREIGN PATENT DOCUMENTS

| | | |
|---|---|---|
| JP | 62019539 A * | 1/1987 |
| JP | 06-002682 B1 | 1/1994 |

OTHER PUBLICATIONS

International Preliminary Report on Patentability and Written Opinion of PCT/US2009/066812 mailed on Jun. 16, 2011, 6 pages.

* cited by examiner

ACETYLENE PROCESS GAS PURIFICATION METHODS AND SYSTEMS

CROSS-REFERENCES TO RELATED APPLICATIONS

This application is a nonprovisional of, and claims the benefit of the filing date of, U.S. Patent Application No. 61/120,261, entitled "Acetylene Process Gas Purification Methods and Systems," filed Dec. 5, 2008. This application is related to co-assigned U.S. Pat. No. 7,314,506, issued Jan. 1, 2008, entitled "Fluid Purification System with Low Temperature Purifier," the entire contents of which are herein incorporated by reference for all purposes.

FIELD OF THE INVENTION

Fluid purification systems and methods are described for producing purified process gases for applications such as the semiconductor fabrication processes. The systems and methods include cooling an unpurified starting gas to separate impurities into liquid phase onto a purifying medium and leaving a purified gas for the application. Techniques and purifier components provide for the disposal of the condensed impurities without interrupting the flow of the purified gas to the application.

BACKGROUND OF THE INVENTION

In many applications for purified process gases there is an increased need for higher levels of purity. This need is acutely felt in the semiconductor fabrication industry, where increasing control and precision in the processing environment require electronic gases that are exceedingly pure. However, the demand for higher purity gases has to be balanced with the cost and reliability of the systems used to supply those gases.

For example, the semiconductor industry needs increasingly pure sources of acetylene gas to fabricate carbon containing components such as dielectric films and photolithographic masks. Acetylene is filled in cylinders containing a porous substance saturated with solvent, such as acetone or dimethylformamide (DMF). The solvent in conjunction with the porous substance increases the capacity of the storage cylinders and helps stabilize the gas by dissolving acetylene gas. However, when the acetylene is discharged from the cylinders, vapors of the solvent also accompany the acetylene gas. The solvent vapors are the largest component of impurities, among other impurities in acetylene gas. Moreover, as the acetylene is being removed from the storage cylinder its concentration in the cylinder drops relative to the concentration of the solvent. This results in an increasing concentration of the solvent impurities in the starting acetylene over the lifetime of the cylinder. The solvent impurity along with its increasing concentration over time in the acetylene gas leads to upsets in certain semiconductor fabrication processes that use acetylene gas. Since the semiconductor fabrication processes are very sensitive to the changing concentration of solvent impurity in the acetylene gas, the cylinder usage is limited to the region where solvent concentration is low and constant in the gas, which results in frequent cylinder change outs and waste of gas.

In certain cases, the acetylene gas stored in cylinders could be passed through an on-site filter to remove solvent impurities before being used in an application. The filters are placed downstream of the storage cylinder and designed to remove the solvents so that only purified acetylene gas reaches the fabrication application. Delivering purified acetylene with consistently low solvent impurities is challenging because the amount of the impurities that need to be removed is significant, and changes over time. Thus, the purifier has to accommodate changing impurity levels in the starting acetylene to produce a purified gas with a constant low level of the impurities.

Because the solvent impurities are intentionally added to the acetylene, they are present in relative large quantities in the source gas, which places significant stress on the purifier to keep the impurity concentrations low in the purified product. It is typical for the purifier material to saturate or be consumed before an application run has been completed, forcing the run to shut down prematurely to regenerate or replace the purifier. These shut downs cause a significant decrease in the productivity of the fabrication process. As the thresholds for acceptable impurity levels keep going lower, the shut downs become more frequent. Thus, there is a need for new methods and systems to produce highly pure process gases with constant low levels of solvent impurities, decreasing frequency of cylinder change-outs, and increasing usage of the stored gases. These and other problems are presently addressed.

BRIEF SUMMARY OF THE INVENTION

Acetylene purification methods and systems are described that permit accumulating liquid impurities to be removed (e.g., drained) from a purification unit without interrupting the flow of purified acetylene. This reduces the amount of down time for processes that consume the purified acetylene, such as electronic semiconductor fabrication processes.

The methods and systems may also be responsive to the rate at which the impurities separate from the source acetylene and adjust the impurity removal rate to keep the impurity concentration at a constant low level in the purified acetylene gas. This can be beneficial when purifying acetylene from a storage cylinder where the acetylene is stored under pressure with a solvent that provides the bulk of the liquid impurities. A full storage cylinder has a higher ratio of acetylene to solvent impurity than a cylinder approaching empty, and this is reflected in an increasing concentration of the impurity in the acetylene flow as the cylinder is emptied. The methods and systems can respond to the increasing impurity concentration in the source acetylene by removing the separated liquid impurities at an increased rate.

The liquid impurities may be removed by passing them through an outlet in a purification container (or downstream of the container) that is intermittently or continuously open while acetylene flows through the container. Gravity or a pressure gradient, or both pull the liquid impurities through the outlet to keep the purification container from becoming oversaturated with the liquid. Because the liquids are removed during purification operations, there is no need to periodically stop the acetylene flow to drain the liquid contaminants from the purification container.

Embodiments of the invention include methods of purifying an acetylene process gas. The methods may include the steps of providing an acetylene source vessel containing acetylene mixed with a solvent impurity, and flowing the source acetylene through a purification container that holds a cooled purifying medium, where at least a portion of the solvent impurity in the source acetylene separates out as a liquid impurity on the purifying medium. The methods may also remove the liquid impurities from the purification container and flowing a purified acetylene gas from the purification container. The purified acetylene gas can have a concentration of the solvent impurity of about 5 vol. % or less, and the separated liquid impurity may be removed while the purified acetylene gas flows from the purification container to keep the concentration of the solvent impurity substantially constant in the purified acetylene gas.

Embodiments of the invention may also include systems for purifying an acetylene process gas. The systems may include an acetylene vessel containing source acetylene mixed with a solvent impurity, and a purification container fluidly coupled to the acetylene vessel. The purification container may contain a purifier medium upon which at least a portion of the solvent impurity in the source acetylene separates out as a liquid impurity. The systems may also include a temperature control system thermally coupled to the purification container, where the temperature control system lowers the temperature of the purifier medium to promote the separation of the solvent impurity as a liquid on the purifier medium. A flow control device may be formed on the purification container or downstream of the container to allow the passage of the separated liquid impurity out of the purification container while the source acetylene flows into the purification container. The flow control device is selected from the group consisting of but not limited to, an orifice, a needle valve, a mass flow controller, a check valve, a regulator, and a ball valve. The flow control device may be coupled to a vent channel outside the purification container that facilitates the liquid impurity flowing out of the purification container. The system may still further include an outlet formed in the purification container through which the purified acetylene gas passes. The purified acetylene gas may have a concentration of the solvent impurity of about 5 vol. % or less, and the separated liquid impurity may be removed while the purified acetylene gas flows from the purification container to keep the concentration of the solvent impurity substantially constant in the purified acetylene gas.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Systems and methods are described for purifying acetylene gas by separating vapor and/or aerosol phase impurities as a liquid from the gas over a cooled purifying medium and removing the liquid impurities from the purification equipment without interrupting the supply of the purified acetylene. These systems and methods may be used to purify acetylene sourced from high-pressure gas storage cylinders that contain a solvent medium such as acetone or dimethylformamide to dissolve and stabilize the stored acetylene. Solvent impurities that accompany the acetylene into the purification container may be separated from gaseous acetylene into a liquid phase in the cold purification container. The purification container is configured with flow-controlled opening that allows the liquid phase impurities to drain from the container without interrupting the acetylene flow through the container.

Figure 1:
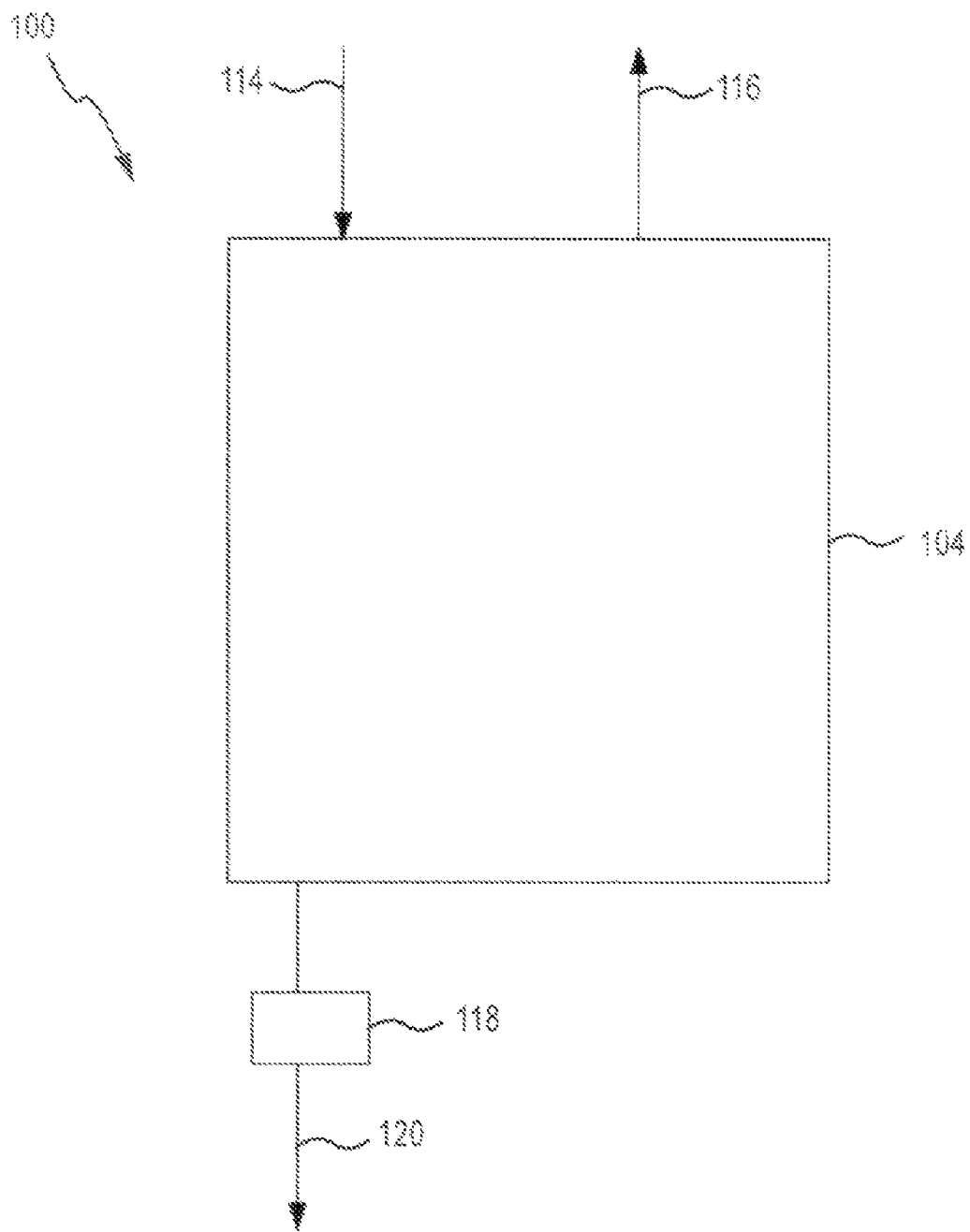
FIG. 1 is a simplified schematic drawing of an acetylene gas purifier according to embodiments of the invention.

FIG. 1 shows a simplified schematic of an acetylene purifier system 100 according to embodiments of the invention. The purifier system 100 includes a purification container 104 that is operable to be cooled to a temperature below room temperature (e.g., from about 0° C. to about −200° C.). The purification container 104 may hold a high-surface area purifier material (not shown) that is also cooled to the temperature of the container 104. The purifier material exposed to the source acetylene provides surfaces for separating the liquid impurities (e.g., solvent impurities) from the acetylene gas.

Source acetylene containing solvent impurities may be introduced to the purification container 104 through fluid inlet 114 that can be reversibly coupled to the acetylene source (not shown). The source acetylene decreases in temperature while flowing through the purification container 104, causing the solvent impurities to separate out as liquid impurities from the acetylene as the acetylene remains in the gas phase. The liquid impurities may be pulled by gravity to the bottom of container 104, where they exit the container 104 through flow control device 118 and conduit 120. Meanwhile, the purified acetylene gas exits the purification container 104 through outlet 116, where it may be transported to the end use application (not shown).

Figure 2:
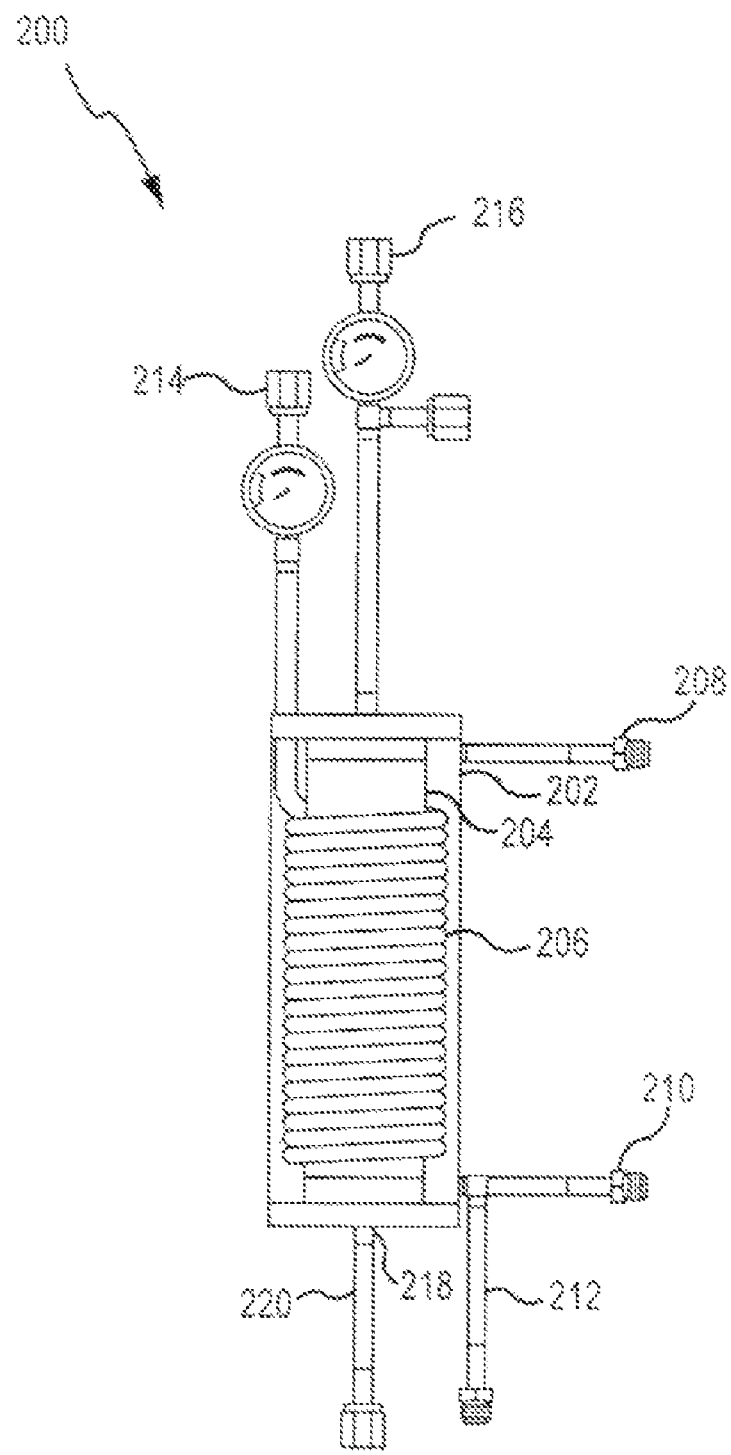
FIG. 2 is a schematic drawing of an acetylene gas purifier according to embodiments of the invention.
Figure 3:
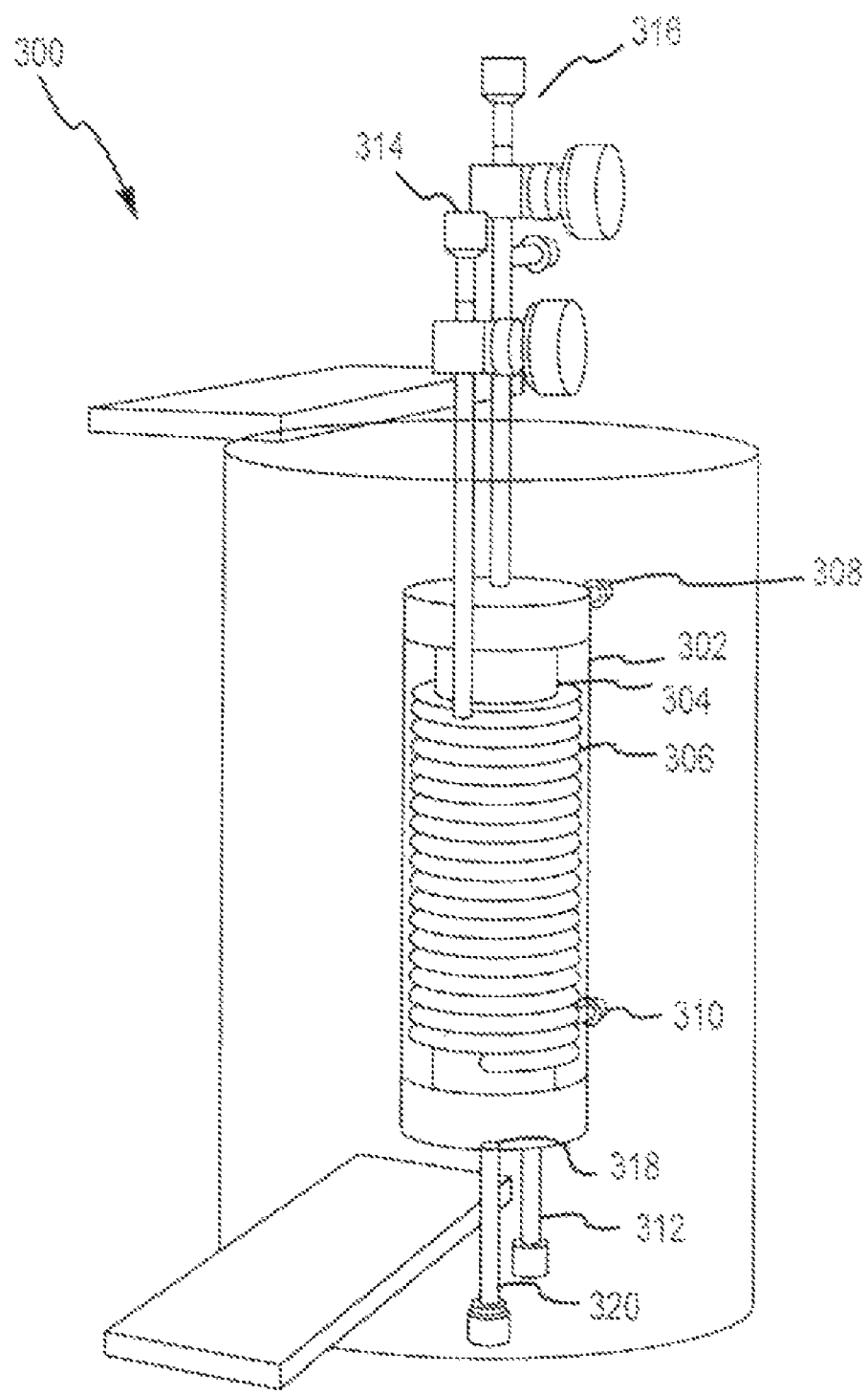
FIG. 3 is a three-dimensional drawing of an acetylene gas purifier according to embodiments of the invention.

FIG. 2 shows an example of an acetylene purifier 200 according to additional embodiments of the invention. FIG. 3 provides a three-dimensional view of the purifier 200. The purifier 200 in FIG. 2 includes an outer cooling container 202 that holds internal container 204 around which gas flow tube 206 is coiled. The cooling container 202 has a coolant inlet 210 and outlet 208 through which a coolant can circulate to maintain the gas flow tube 206 and internal purification container 204 at a temperature below ambient. The coolant inlet 210 and outlet 208 may be reversibly coupled to a circulating source of coolant fluid (not shown). The coolant outlet 208 may also be coupled to an auxiliary outlet 212 for draining residual coolant from the cooling container 202, among other functions.

Source acetylene may be introduced into the gas flow tube 206 through gas inlet 214 that can be reversibly coupled to an acetylene source (not shown). The source acetylene cools while flowing through the coiled gas flow tube 206 and the solvent impurities can start to separate from the acetylene gas into a liquid phase. The separation of impurities into a liquid phase may continue as the acetylene flows from the gas flow tube 206 into the internal purification container 204 due to the presence of the cooled purifying medium and the liquid impurity collects in the purification container 204, and the purified acetylene gas flows to gas outlet 216. The gas outlet 216 may be reversibly coupled to an application (not shown) that uses the purified acetylene gas.

The liquid impurities collecting in the purification container 204 migrate to the bottom of the container. A flow control device 218 may be formed in the purification container 204, or downstream of the container, to remove the impurities from the purifier 200. The flow control device 218 may be coupled to a conduit 220 that defines a vent channel for facilitating the exit of the liquid impurity from the purification container 204. The conduit 220 may be coupled to a vacuum source (not shown) that maintains a lower pressure on the conduit side of the flow control device 218 than the purification container 204 side. This establishes a decreasing pressure gradient that helps pull fluid impurities from inside the purification container 204 to the vent channel in conduit 220. In some instances the pressure and temperature conditions in the vent channel may cause the liquid impurities to vaporize back into the gas phase, allowing the impurities to be vented from the purifier system with or without the help of a carrier gas.

Examples of the flow control device 218 may include without limitation, an orifice, a needle valve, a mass flow controller, a check valve, a regulator, and a ball valve, among other devices. When the flow control device 218 is an orifice, the orifice may have a variety of shapes and sizes. For example the orifice may be circular, elliptical, polygonal, etc. The flow control device 218 may be configured to prevent liquid impurities from accumulating in the purification container 204 at peak rates of separation of the impurities (usually at or near the endpoint of emptying an acetylene gas cylinder). Thus, the flow control device 218 is configured to accommodate a varying removal rate of the impurities and keep the removal rate above an accumulation threshold where the liquid impurities form so rapidly that they begin to collect upstream of the flow control device 218 in the purification container 204. The flow control device 218 may also be configured to reduce the amount of acetylene that is diverted from the application by instead passing through the conduit 220 with the liquid impurity. Embodiments size the orifice to have a cross-sectional area in the bottom surface of container 204, or downstream of the container 204, of about $8 \times 10^{-9}$ cm$^2$ to about 1 cm$^2$. For example, a circular shaped orifice may have a diameter of about 1 μm to about 1 cm (e.g., about 1 μm to about 1 cm, about 10 μm to about 100 μm, about 50 μm, etc.).

The flow control device 218 may be set to keep the liquid impurities flowing continuously into the waste stream while the purified acetylene is being delivered to the application. Alternatively, the flow control device 218 may permit periodic release of the liquid impurities into the waste anytime before they accumulate in the purification container 204 to a point where impurity levels start to increase in the purified acetylene exiting through gas outlet 216. In both cases, the removal of the impurities during the operation of the purifier can substantially reduce or eliminate the amount of down time required for draining, cleaning, and recharging the purification container 204.

Reducing or eliminating the accumulation of the liquid impurities in the purification container 204 permits the purifier to provide a purified acetylene gas with low levels of solvent impurities over the life of an acetylene storage cylinder. Even as the percentage of solvent impurities in the source acetylene increases over the life of the cylinder (e.g., from starting with about 0.05 to 0.5 vol. % of the solvent impurity and finishing with about 5 to 10 vol. % or more), the purified acetylene is maintained with a relatively constant low level of these impurities (e.g., about 5 vol. % or less, about 1 vol. % or less, about 4000 ppm to about 10 ppm, by vol., etc., of solvent impurity in the purified acetylene).

Figure 4:
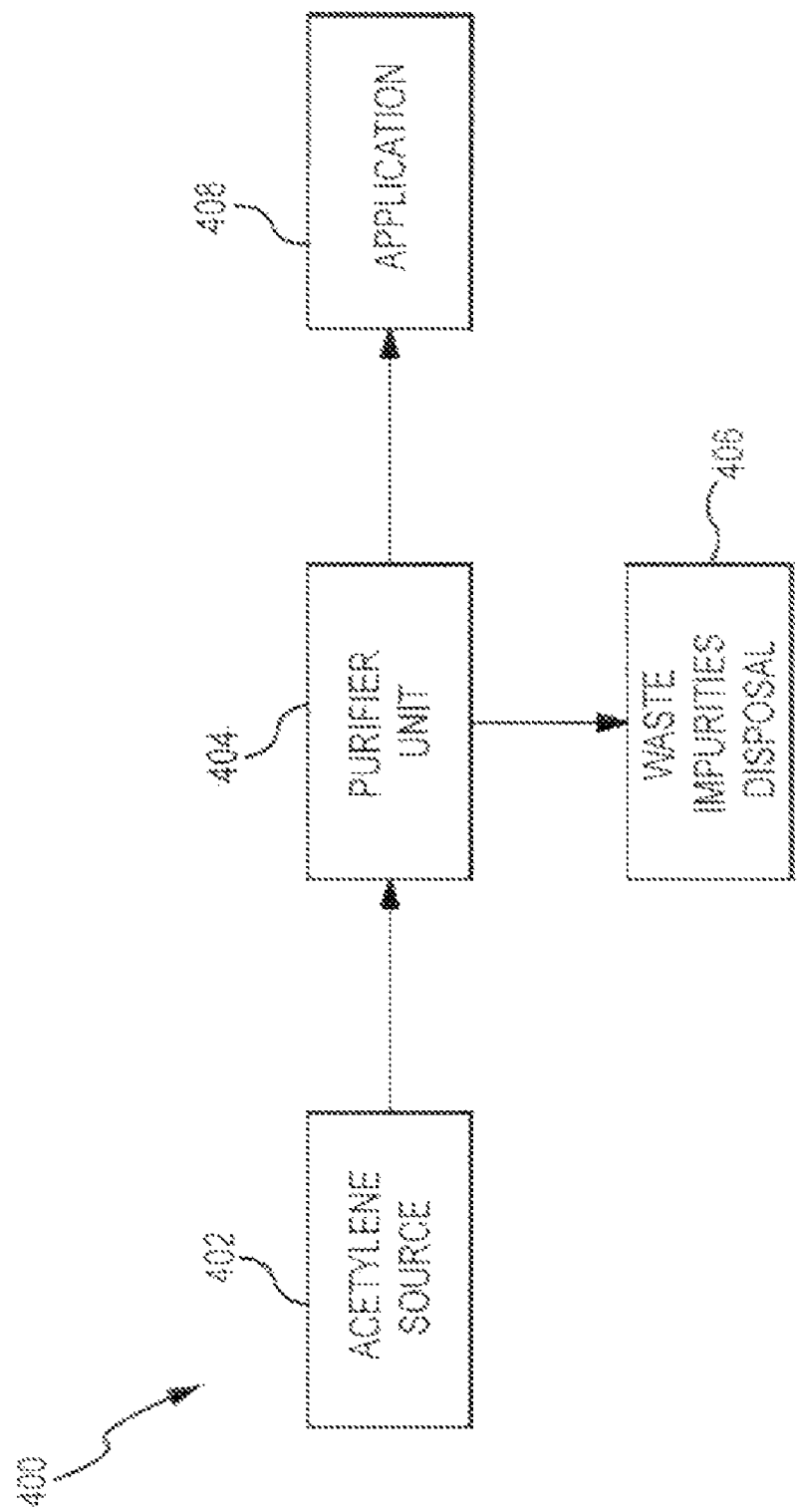
FIG. 4 shows a simplified schematic drawing of a system to supply purified acetylene gas to an application according to embodiments of the invention.

Referring now to FIG. 4, a simplified schematic drawing of a system 400 to supply purified acetylene gas to an application according to embodiments of the invention is shown. The system 400 includes an acetylene source 402, such as a high-pressure acetylene cylinder, that contains an unpurified mixture of acetylene and solvent impurity. The source acetylene is sent to purifier unit 404 which includes a low-temperature purifier unit similar to purifier described in FIGS. 1-3 above. As the source acetylene cools moving through the purifier, the solvent impurity separates from the acetylene into a liquid phase. The liquid impurities are removed from the purifier unit 404 by passing through a flow control device to a waste disposal unit 406. The flow control device may be coupled to a conduit that opens into a vent channel in waste disposal unit 406 that is maintained at a reduced pressure resulting in the re-evaporation of the liquid impurities.

As the liquid impurities travel from the purifier unit 404 to the waste disposal unit 406, a flow of purified acetylene with a significantly reduced concentration of the impurities passes to an application 408. The application 408 that consumes the purified acetylene may include a semiconductor fabrication process application such as making an ashable hard mask for patterning an integrated circuit.

Figure 5:
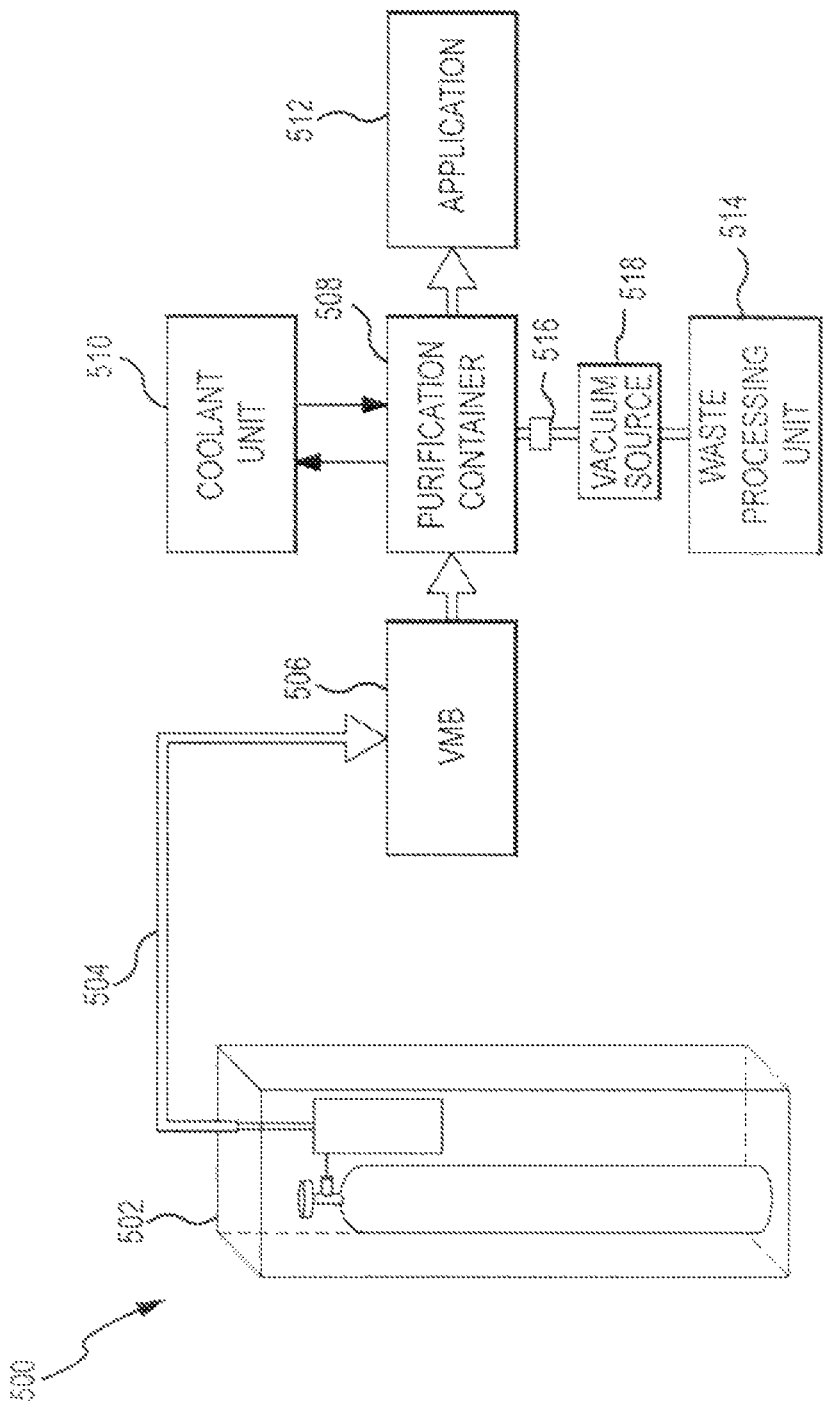
FIG. 5 shows a simplified schematic drawing of a system to supply purified acetylene gas to an application according to additional embodiments of the invention.

FIG. 5 shows a simplified schematic drawing of a system 500 to supply purified acetylene gas to an application according to embodiments of the invention. System 500 shows a stored acetylene source 502 in the form of a high-pressure acetylene gas cylinder. The acetylene is stored in the cylinder with a solvent, such as acetone or dimethylformamide which dissolves and helps maintain the stability of the acetylene during the storage period. In the embodiment shown, the acetylene gas cylinder is housed in a cabinet which may include ventilation conduits, gas sensors, and controllers that permit a system operator to control system operations such as gas shut off, flow rates, etc.

The source acetylene gas exits the acetylene source through supply conduit 504 for purification in the low-temperature purification unit 508. In system 500, the flow rate and pressure of source acetylene reaching the purification unit 508 is controlled by a valve manifold box (VMB) 506. In the embodiment shown, the VMB 506 is separate from both the acetylene source 502 and the purification unit 508. In additional embodiments, VMB 506 may be integrated into the acetylene source 502 (e.g., integrated into the gas cabinet) or the purification unit 508 (e.g., directly coupled to an inlet gas flow tube of the purifier).

The source acetylene moves through the cooled purification unit 508 and a portion of the solvent impurity separates from the acetylene into a liquid phase. Coolant fluid is cycled through the purification unit 508 by a separate coolant unit 510 fluidly coupled to the purification unit. In additional embodiments (not shown) a coolant unit may be integrated with the purification unit.

The purification unit 508 separates the source acetylene into a purified gas sent to the application 512 and the liquid impurities (primarily solvent impurities) sent to a waste processing unit 514. As noted above, the liquid impurities may pass through a flow control device 516 in a container that collects liquid impurities from the chilled acetylene gas stream over the purifying medium. The flow control device 516 may be formed in the container or downstream of the container where the force of gravity and/or pressure gradient draws the liquid impurities. In the embodiment shown, a flow control device 516 controls the rate of impurity removal from the container. Examples of flow control device 516 may include an orifice, mass flow controller, needle valve, and/or other device to control the flow rate of impurities exiting the purification unit 508. A vacuum source 518 may also be coupled to the flow control device 516 to create decreasing pressure gradient that accelerates the flow of liquids exiting the purification unit 508 through the flow control device 516. The vacuum source 518 may also create a low-pressure region downstream of the flow control device 516 that re-vaporizes the liquid impurities allowing their transportation from system 500 in the gas phase.

Figure 6:
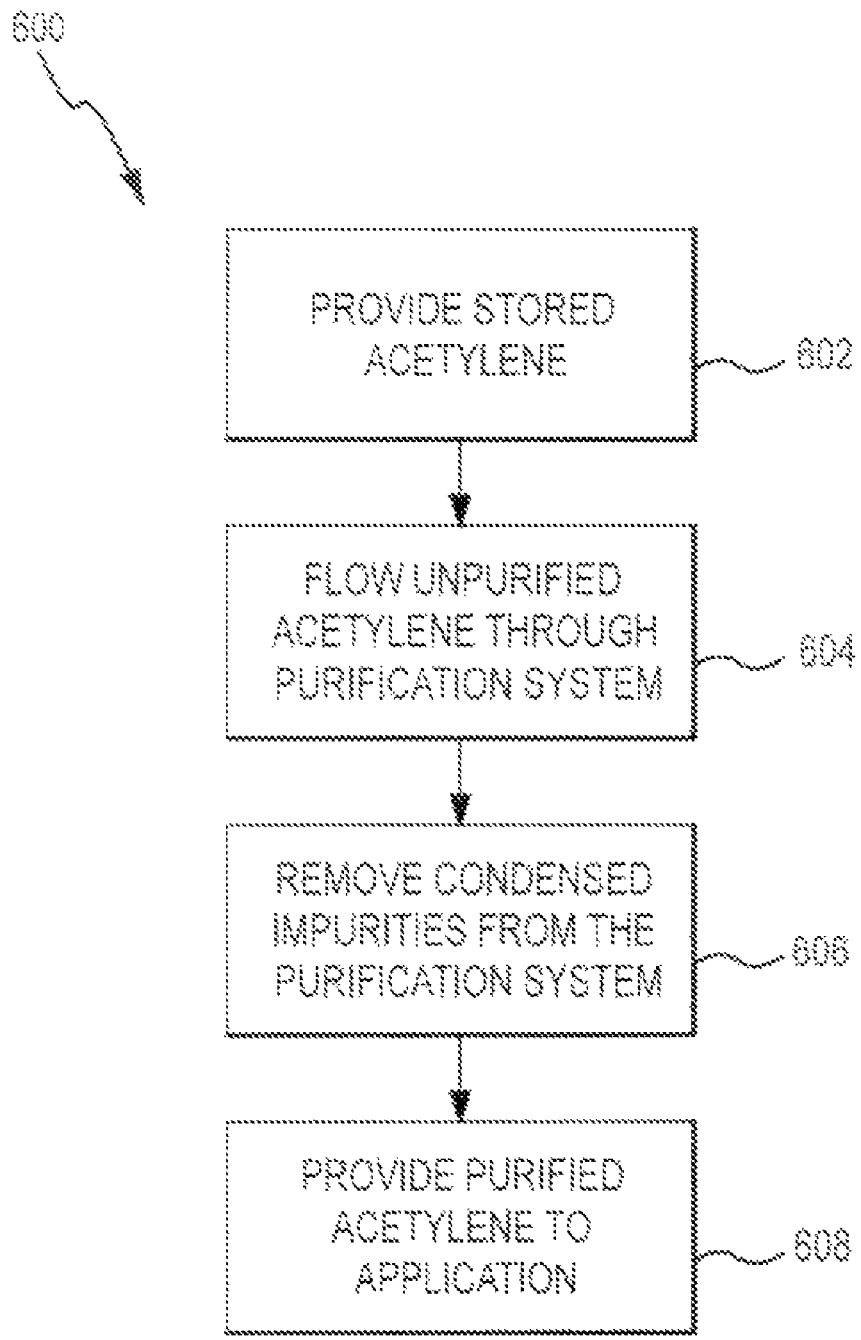
FIG. 6 shows a flowchart of selected steps in a method of purifying an acetylene process gas according to embodiments of the invention.

FIG. 6 shows selected steps in a method 600 of purifying an acetylene process gas according to embodiments of the invention. The method 600 includes the step of providing a stored acetylene source 602. The provided acetylene source may be a high-pressure acetylene gas cylinder that also includes a solvent that dissolved and helps to stabilize the acetylene during storage. The source acetylene released from the acetylene source is allowed to flow through a purification system 604. The gas flow rate and pressure of these releases may be regulated by, for example, pressure regulators, mass flow controllers, and/or needle valves, among other equipment, to maintain a substantially constant gas pressure in the purification system.

The purification system itself may include a low-temperature purifier that separates solvent impurities into a liquid phase that is separated from the acetylene remaining in the gas phase. The liquid phase impurities may be removed from the purification system 606 while the purified acetylene produced by the system is provided to the end use application 608. The concurrent removal of liquid impurities and supply of purified acetylene may be accomplished by providing an outlet (e.g., a flow control device) in a purification container or downstream of the container that allows the liquid impurities to drain from the container as acetylene gas flows through the container. The container is maintained at a constant low temperature (e.g., about 0° C. to about −200° C., about −20° C. to about −50° C., about −45° C., etc.) through contact with a coolant fluid at an external surface of the container. The coolant fluid may be circulated around the container carrying away heat energy from the container to maintain a substantially constant low temperature inside the container.

By maintaining the acetylene gas at a constant pressure and temperature in the purification container of the purification system, a purified acetylene gas can be supplied to the end use application with a constant and consistent low level of solvent impurities. For example, the purified acetylene gas may have a residual level of solvent impurities of about 5 vol. %, 4 vol. %, 3 vol. %, 2 vol. %, 1 vol. %, 0.5 vol. %, 4000 ppm, 3000 ppm, 2000 ppm, 1000 ppm, 500 ppm, 250 ppm, 100 ppm, 50 ppm, 25 ppm, 10 ppm, by vol., etc. Variation in the impurity concentration for the purified acetylene is reduced by removing liquid impurities from the purification unit during operation. This prevents the accumulation of liquid impurities to a level where the purifier becomes saturated and has difficulty separating additional solvent impurities from the acetylene gas stream.

In addition, the impurity removal process is designed to accommodate varying rates of liquid impurity production in the purification system. As noted above, the concentration of solvent impurity from an acetylene gas source can change significantly over the lifetime of the source. For acetylene stored in a high-pressure gas storage cylinder, the concentration of solvent impurities can increase from about 0.05 vol. % to about 10 vol. % or more at the end of the cylinder's supply. The impurity removal process can accommodate this many-fold increase in solvent impurity concentration by allowing the liquid solvent impurities to drain from the purification system at an increased rate over time to maintain a zero or low level of liquid accumulation in the purification container, and consequently a consistently low level of impurities in the purified acetylene.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the impurity" includes reference to one or more impurities and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of purifying an acetylene process gas, the method comprising:
    providing an acetylene vessel comprising source acetylene mixed with a solvent impurity;
    flowing the source acetylene through a purification container that holds a cooled purifying medium, wherein at least a portion of the solvent impurity in the source acetylene separates out as a liquid impurity on the purifying medium; and
    removing the separated liquid from the purification container; and
    flowing a purified acetylene gas from the purification container, wherein the purified acetylene gas has a concentration of the solvent impurity of about 5 vol. % or less, and wherein the separated liquid impurity is removed while the purified acetylene gas flows from the purification container to keep the concentration of the solvent impurity substantially constant in the purified acetylene gas.

2. The method of claim 1, wherein the concentration of the solvent impurity in the purified acetylene gas is about 1 vol. % or less.

3. The method of claim 1, wherein the separated liquid is removed by passing the liquid through a flow control device formed in the container.

4. The method of claim 1, wherein the separated liquid is removed by passing the liquid through a flow control device coupled to the container.

5. The method of claim 4, wherein the flow control device is selected from the group consisting of an orifice, a needle valve, a mass flow controller, a check valve, a regulator, and a ball valve.

6. The method of claim 1, wherein the solvent impurity is selected from the group consisting of acetone and dimethylformamide.

7. The method of claim 1, wherein the substantially all of the acetylene is removed from the acetylene vessel without interrupting the flow of the source acetylene through the purification container.

8. The method of claim 4, wherein a flow rate of the liquid impurity through the flow control device increases with an increase in separation rate of the solvent impurity on the purifying medium.

9. The method of claim 1, wherein a concentration of the solvent impurity increases over time as more of the source acetylene is removed from the acetylene vessel.

10. The method of claim 1, wherein the concentration of the solvent impurity in the source acetylene increases from about 0.05 vol.% to about 10 vol.%.

11. The method of claim 1, wherein the source acetylene gas is maintained at a constant temperature and pressure in the purification container.

12. The method of claim 4, wherein the liquid impurity is converted into a vapor after passing through the flow control device.

13. The method of claim 12, wherein the vapor exhausted through a vent channel.

14. The method of claim 1, wherein the liquid impurity is dispensed in the liquid phase.

15. The method of claim 4, wherein the liquid impurity is intermittently removed from the purification container through the flow control device.

16. The method of claim 1, wherein the purified acetylene gas is transported to a semiconductor processing system that is coupled to the purification container.

* * * * *